(12) United States Patent
Teo

(10) Patent No.: US 6,432,120 B1
(45) Date of Patent: Aug. 13, 2002

(54) LANCET ASSEMBLY

(75) Inventor: Hock Meng Teo, Singapore (SG)

(73) Assignee: Surgilance PTE Ltd. (SG)

( * ) Notice: Subject to any disclaimer, the term of this patent is extended or adjusted under 35 U.S.C. 154(b) by 0 days.

(21) Appl. No.: 09/565,896

(22) Filed: May 5, 2000

(30) Foreign Application Priority Data

Jun. 18, 1999 (SG) ......................................... 9902934-0

(51) Int. Cl.$^7$ .............................................. A61B 17/34
(52) U.S. Cl. ...................................... 606/182; 606/181
(58) Field of Search ................................ 606/181–185; 600/583

(56) References Cited

U.S. PATENT DOCUMENTS

| | | | |
|---|---|---|---|
| 4,616,649 A | | 10/1986 | Burns |
| 4,817,603 A | * | 4/1989 | Turner et al. .............. 606/182 |
| 4,869,249 A | | 9/1989 | Crossman et al. |
| 5,026,388 A | * | 6/1991 | Ingalz ....................... 606/182 |
| 5,366,470 A | * | 11/1994 | Ramel ...................... 606/183 |
| 5,439,473 A | * | 8/1995 | Jorgensen |
| 5,540,709 A | * | 7/1996 | Ramel ...................... 606/182 |
| 5,628,765 A | * | 5/1997 | Morita ....................... 606/182 |

FOREIGN PATENT DOCUMENTS

| | | |
|---|---|---|
| EP | 0403873 A1 | 12/1990 |
| WO | WO 93/09723 | 5/1993 |

* cited by examiner

Primary Examiner—Michael J. Milano
Assistant Examiner—Daniel Jacob Davis
(74) Attorney, Agent, or Firm—Jon A. Gibbons; Fleit, Kain, Gibbons, Gutman & Bongini P.L.

(57) ABSTRACT

A lancet assembly having a lancet holder and a triggler enclosing a lancet structure. The triggler is partially inserted into a lancet holder from the distal end. The holder is provided with a rigid internal spring holder to receive the spring-loaded lancet structure. The lancet structure is provided with a body coupled to a spring which extend from the proximal end of the body. The spring has a linear axis of compression which coincide with the longitudinal axis of the lancet assembly. A lancet is attached to the body with the sharp tip pointing towards the distal end. The triggler interacts with the lancet holder via a triggering element to maintain the spring in a compressed state such that the lancet structure is in a stable standby position which is not easily triggered by accidental bumps on the assembly.

11 Claims, 4 Drawing Sheets

LANCET ASSEMBLY

FIELD OF THE INVENTION

The present invention is related to finger-pricking devices. In particular, the present invention is related to lancets for medical use.

BACKGROUND OF THE INVENTION

Lancets or finger-pricking devices is widely used in the medical field for applications such as skin incisions and blood drawing. In some lancet assemblies, the blade or needle is kept in a standby position until it is triggered by the user, who is typically a medical personnel in charge of drawing the blood from a patient. In other lancet assemblies, the user has to manually set the assembly to an armed position before firing can be triggered. Upon triggering, the blade fires onto the skin of the patient, for example on the finger, and makes an incision.

Such lancet assemblies must be sterilized before use, and the lancet maintained under sterile conditions until use. Furthermore, the lancet assembly should be disposable to eliminate the chances of disease transmission due to the blade being used on more than one person. In this regard, the lancet should ideally be designed for only one firing, and have safety features to prevent reuse. Other features which are desirable include safety features to reduce the chance of the lancet accidentally misfiring and pricking someone.

It is therefore an object of the present invention to provide a safe and reliable lancet assembly.

SUMMARY OF THE INVENTION

Figure 1:
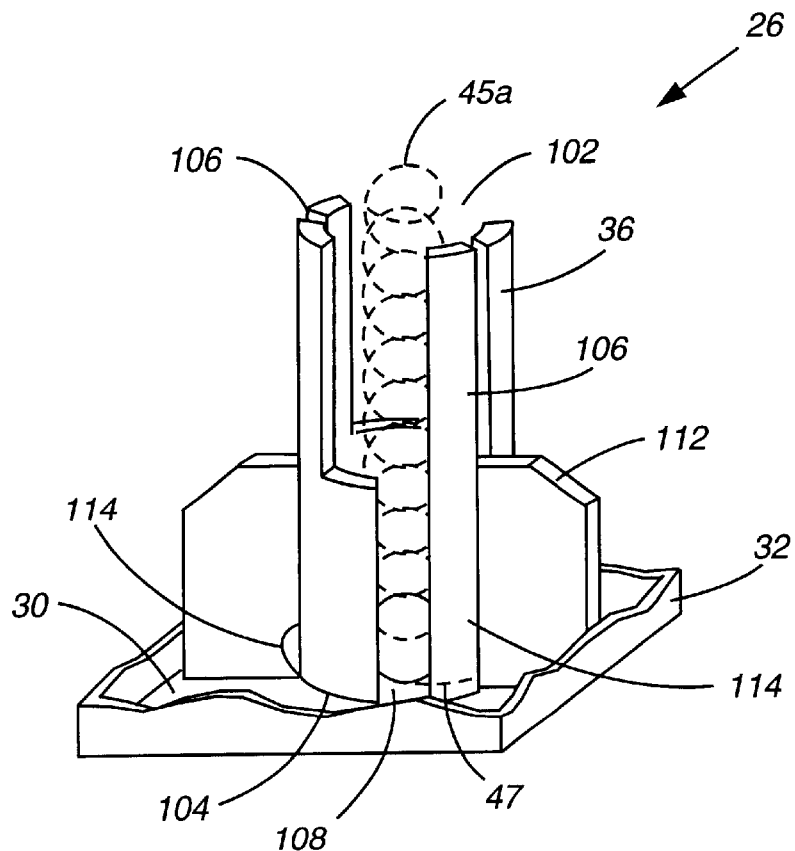
FIG. 1 is a perspective view of the triggler in FIG. 1 with the side walls cut away to expose the internal features.

Accordingly, the present invention provides in one aspect a lancet assembly having a distal end, a proximal end and a longitudinal axis running therebetween. The triggler is partially inserted into a lancet holder from the distal end. The lancet holder is provided with a rigid internal spring holder to receive a spring-loaded lancet structure. The lancet structure is provided with a body coupled to a spring which extend from the proximal end of the body. A lancet is attached to the body with the sharp tip pointing towards the distal end. The triggler interacts with the lancet holder via a triggering element to maintain the spring in a compressed state such that the lancet structure is in a stable standby position which is not easily triggered by accidental bumps on the assembly. The standby position is automatically maintained, and an additional arming step is eliminated. In another aspect, the assembly is provided with a safety feature to prevent: tampering of the lancet assembly. In yet another aspect, the spring is secured to the end wall of lancet holder such that dislocation caused by the sudden expansion force of the firing process is prevented. Furthermore, the spring is chosen to over-extend upon firing, such that the sharp tip of the lancet can jab a patient's skin held outside the lancet holder upon firing, but the sharp tip is withdrawn safely back into the lancet assembly when the spring is recoiled into the resting position.

In another aspect, a method is provided for finger pricking using a lancet assembly with a distal end and a proximal end. This lancet assembly contains a lancet with a sharp tip that fires outwards from the distal end when the assembly is compressed inwards from the same distal end. The method involves placing the distal end of the lancet assembly onto a finger to be pricked, and pressing the assembly into the finger from the proximal end. This compresses the assembly and causes firing of the lancet whereby the finger is pricked.

In the preferred embodiment, the lancet holder is provided with an open distal end and a closed proximal end defined by an end wall. Side walls extend from the end walls to form a box-like exterior casing. A mating element, preferably disposed on the interior surface of the side walls, is provided to interact with the triggler. The lancet holder also contains an elongated spring holder having an open first end and a second end attached to and extending from the end wall of the lancet holder. The supporting structures between the first end and the second end define an interior space wherein the lancet structure is received. A receiving element is provided on the spring holder for mating with a guiding element on the lancet structure such that the lancet can move along the longitudinal axis. A securing element is provided near the proximal end of the lancet holder for securing the proximal end of the spring from dislocation during firing.

The triggler contains an end wall for closing the open distal end of the lancet holder. This triggler end wall contains an aperture wherethrough the sharp tip of the lancet fires when triggered. A stabilizing element, extending from the triggler end wall, is inserted between the side walls of the lancet holder and the supporting structures of the spring holder, allowing sliding movement of the triggler relative to the lancet holder along the longitudinal axis. This sliding movement is limited by a safety catch on the triggler which is designed to engage the mating element of the lancet holder such that the triggler is maintained between a standby position and a firing position. A triggering element is also provided in the triggler for engagement with the guiding element of the lancet structure. When the triggler and the triggering element are in the standby position, the guiding element is forced towards the proximal end of the lancet holder, such that the spring is maintained in the standby position of a compressed high potential energy state. When a compression force is applied to the triggler end wall in the direction of the proximal end, the triggering element may be moved into a firing position in which it is disengaged from the guiding element. Once the guiding element is no longer held in the standby position, the potential energy stored in the compressed spring is released and the spring extends, forcing the sharp tip of the lancet structure to fire through the aperture of the triggler end wall.

DESCRIPTION OF THE INVENTION

The lancet assembly according to the present invention has a longitudinal axis defined by the axis of compression of the spring. The triggler (or triggering device) and the lancet holder interact by keeping the spring of the lancet structure in a standby compressed state. Upon compression of the assembly along the longitudinal axis by the user pressing the end wall of the triggler onto the skin of a patient, the lancet will be fired to pierce the skin.

The following detailed description describes the preferred embodiment for implementing the underlying principles of the present invention. One skilled in the art should understand, however, that the following description is meant to be illustrative of the present invention, and should not be construed as limiting the principles discussed herein. In the following discussion, and in the claims the terms "including", "having" and "comprising" are used in an open-ended fashion, and thus should be interpreted to mean "including but not limited to."

FIG. 1 shows an embodiment of the lancet holder 26 with the side walls cut away to reveal the spring holder 36. A spring 45a is shown in dotted line. In this embodiment, the spring holder 36 is generally shaped into a cylinder with an open first end 102, and a second end 104 attached to the end wall 30 of the lancet holder. Two slits 106, running from the open first end towards the proximal end are provided on the side wall of the spring holder. In this embodiment, a wider slot 108 is further cut into the side wall of the spring holder. To strengthen the side walls of the spring holder, two ridges 112 are provided to connect the side walls of the spring holder and the lancet holder. This improves the rigidity of the spring holder, and hence the reliability and accuracy of the firing procedure. An additional pair of lugs 114 is provided at the proximal end of the spring holder juxtaposing the two sides of slot 108. These lugs can interact with a unshaped extension 47 in the spring. The lancet holder is preferably made from a rigid plastic material with good mechanical strength such as polycarbonate material in order to withstand the high energy firing process of the metal spring.

Figure 2:
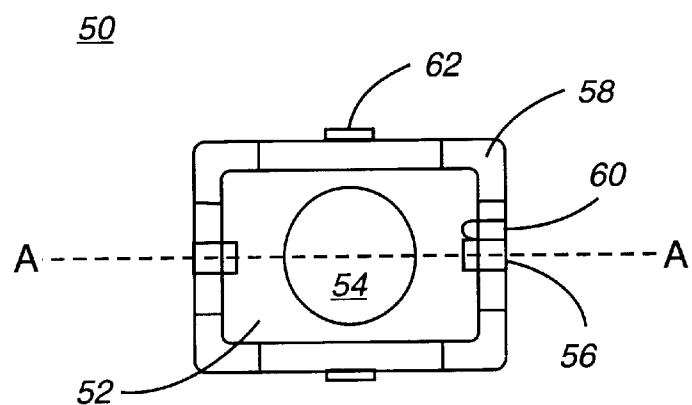
FIG. 2 is the bottom view of the triggler according to the present invention.
Figure 3A:
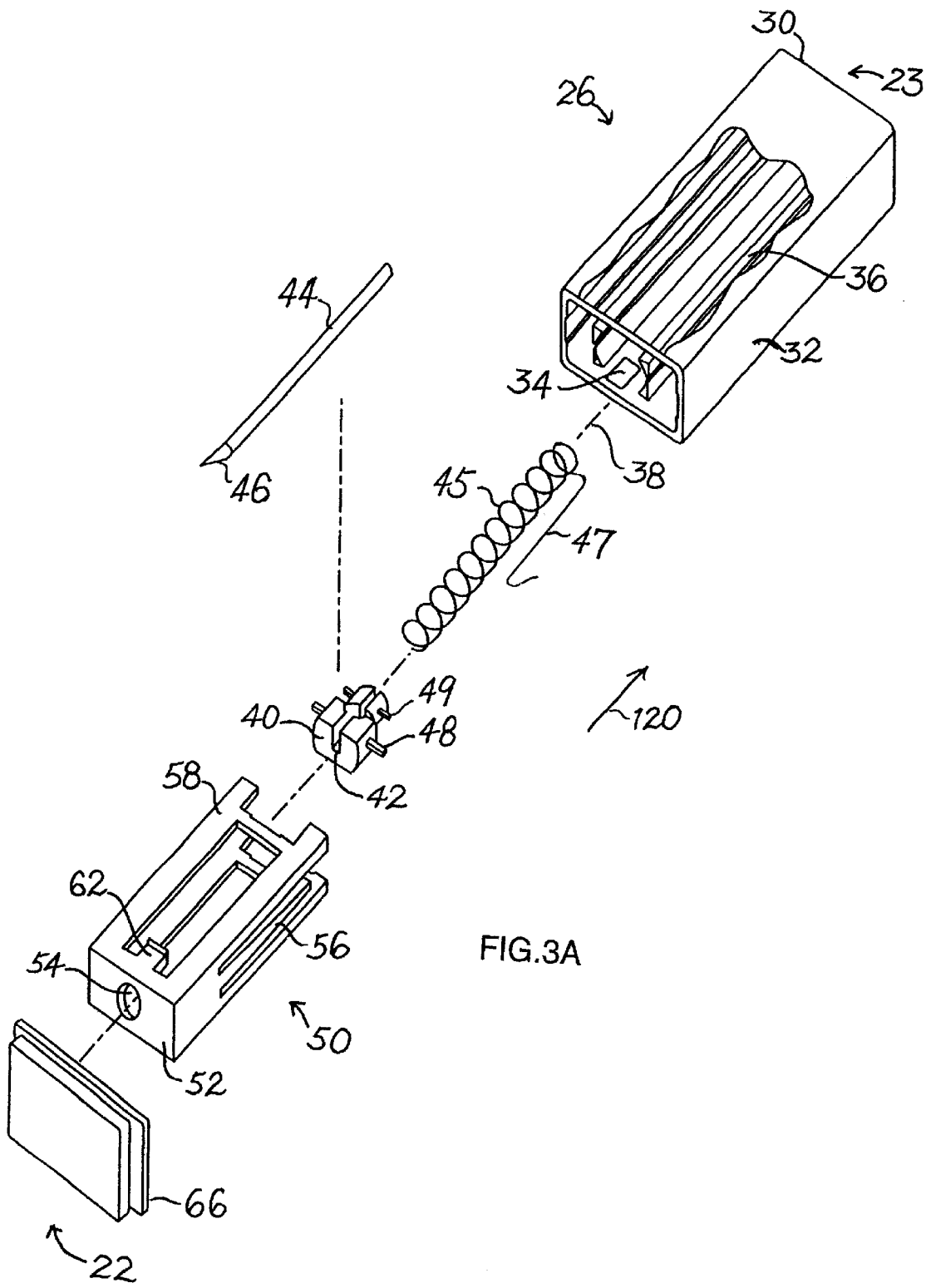
FIG. 3A is an exploded perspective view of the lancet assembly according to the present invention.
Figure 3B:
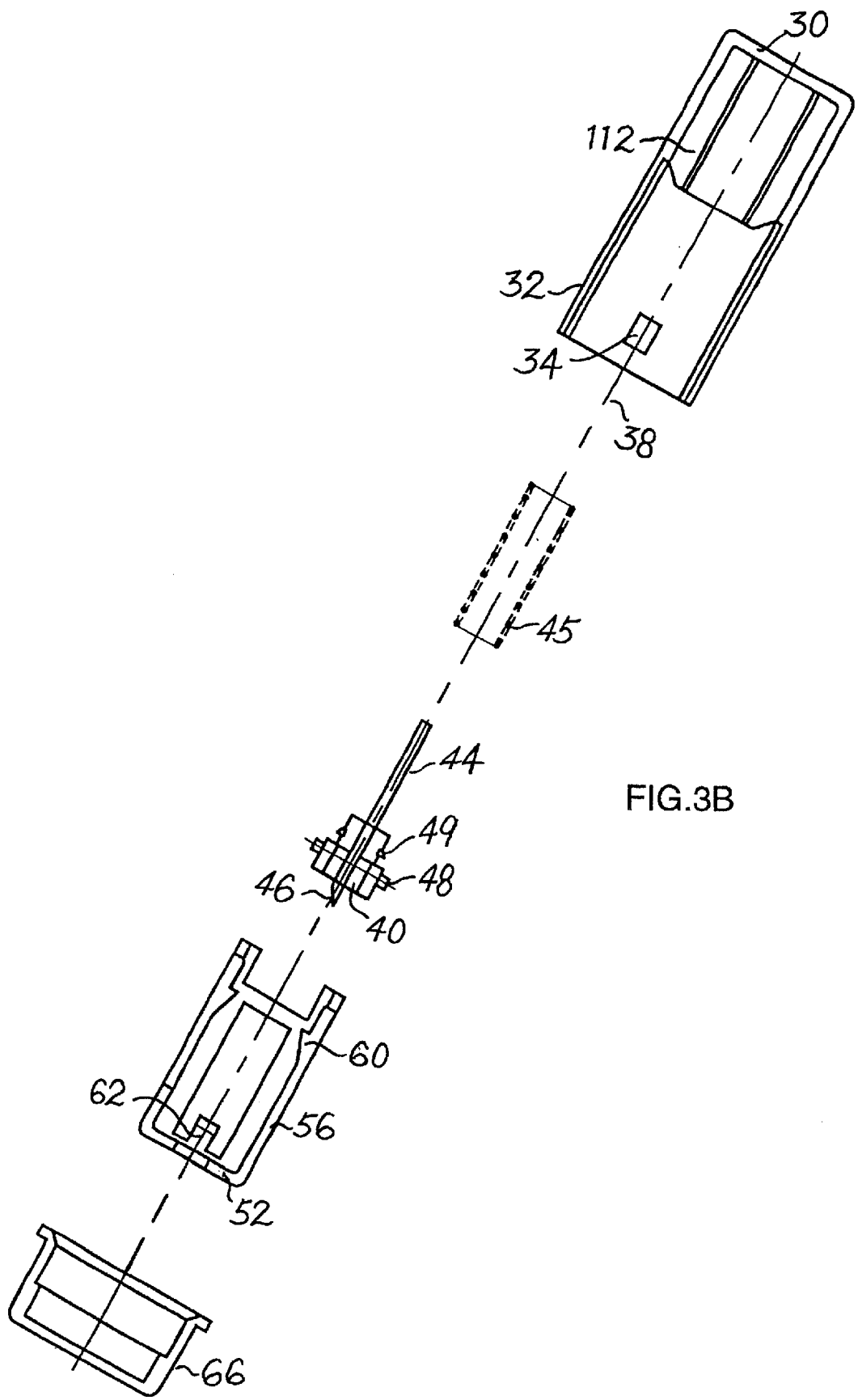
FIG. 3B is an exploded cross-sectional view of the lancet assembly along line A—A according to the present invention.
Figure 4A:
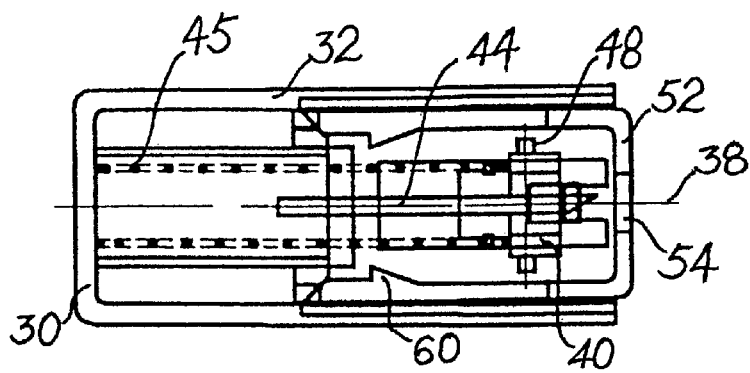
FIGS. 4A and B are longitudinal cross-sectional views along line A—A of the lancet assembly in the after use and firing positions respectively according to the present invention.
Figure 4B:
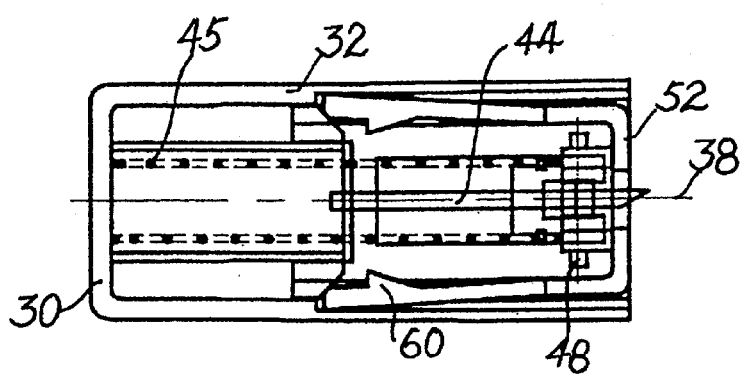
FIGS. 4C and D are longitudinal cross-sectional views along line A—A of the lancet assembly in the standby position with (FIG.4C) or without (FIG.4D) the protective cap according to the present invention.
Figure 4C:
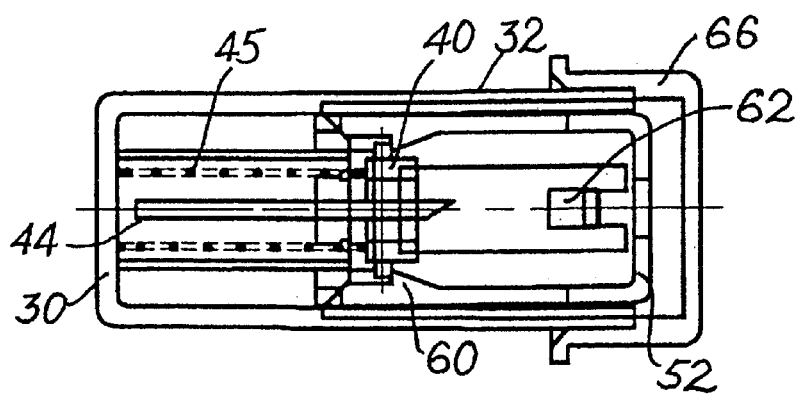
Figure 4D:
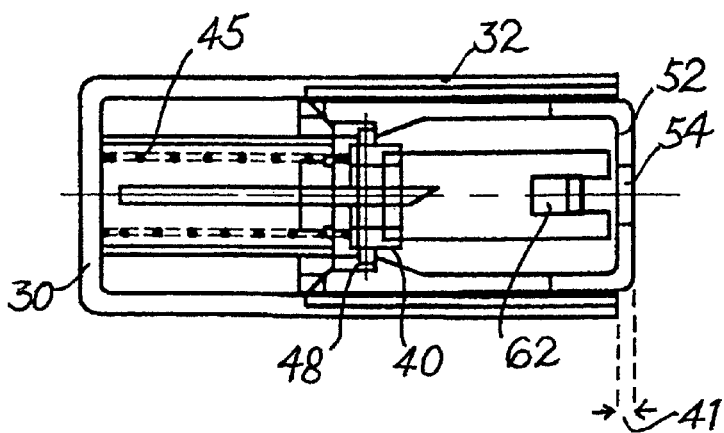

FIG. 2 shows detailed features of the triggler 50. In this embodiment, the triggler is of a rectangular shape having an end wall 52 with aperture 54. Side walls 58 extending from the four corners of end wall 52 to form a stabilizing element. The triggering element, in the form of actuating ribs 56 extends from two opposing sides of end wall 52. A small protrusion, in the form of wedge 60, is provided at the end of each actuating rib 56. Wedge 60 protrudes into the interior of the triggler. Two L-shaped clips 62 further extend from opposing sides of end wall 52. The triggler is preferably made from a slightly flexible plastic, such as Acrylonitrile Butadiene Styrene (ABS) material to allow the actuating ribs to bend with the right resistance.

FIGS. 3A, 3B and 4A–D show how the lancet assembly, having a longitudinal axis 38, a distal end 22 and a proximal end 23, is assembled to provide the desired features. The lancet structure includes a lancet body 40, a lancet 44 with a sharp tip 46, and a spring 45 with a linear axis of compression. In this embodiment, spring 45 is a helical metal coil, and has a U-shaped extension 47 at the proximal end. Lancet body 40 is provided with channel 42 for receiving and securing the lancet such that the sharp tip 46 of the lancet is at the distal end. Guiding pins 48 are provided on opposing sides of body 40. Securing pins 49 extend from the proximal end of body 40 for securing spring 45 onto the body.

The assembled lancet structure is received within spring holder 36 with spring 45 pressed onto end wall 30 of lancet holder 26. Guiding pins 42 are slotted into slits 106 such that lateral movement and rotational movement around the longitudinal axis is prevented. The spring 45 is fitted onto the lancet body 40 such that the U-shaped extension 47 extends through slot 108 and wraps around either one of lug 114. This arrangement prevents the spring from being easily dislocated from the spring holder during the firing process.

The side walls 58 of triggler 50 are slidably inserted into the space between the spring holder 36 and the side walls 32 of the lancet holder such that the small wedges 60 of actuating ribs 56 slide through slits 106 and press the guiding pins towards the proximal end of the lancet holder. The L-shaped clip 62 on the triggler is adapted to engage the elongated recess 34 on the lancet holder to limit the longitudinal movement of the triggler relative to the lancet holder.

During assembly, the triggler is pressed down toward the lancet holder in the direction shown by arrow 120, and in the process, the guiding pins, are forced down concomitantly by the small wedges on the actuating ribs. This compression force compresses the spring. As the triggler is pressed lower, the resistance of the spring to further compression becomes greater. When the resistance of the spring exceeds the mechanical strength of the actuating ribs to push on the guiding pins, the actuating ribs are bent outwards relative to the longitudinal axis of the lancet holder, releasing the compression of the lancet structure and resulting in firing of the lancet.

In the preferred embodiment, a cap 66 is provided to interact with the side walls 32 of the lancet holder to maintain sterility and to protect users in cases of accidental firing. The cap is preferably an air-seal or sterile cap.

In the standby position, the resistance of the spring to compression forces clip 62 towards the distal end of recess 34. In the most preferred embodiment, the length of actuating ribs 56 is designed to allow the end wall of the triggler to extend a short distance 41 from the side walls 32 of the lancet holder when the assembly is in the standby position, for example, 12 mm from the distal end. This short distance means that the triggler is well protected from firing due to accidental bumping. Furthermore, due to the lack of lateral movement, the direction of the external pressure has to be very close to the longitudinal axis of the assembly in order for the triggler to be compressed sufficiently for firing to occur. The mechanical strength of the actuating rib may be designed such that deformation (i.e. firing) only occurs when sufficient pressure is provided on the triggler end wall. In addition, the spring may be chosen such that triggering only occurs when the triggler is flush against the edge of the proximal end of the lancet holder, or even pushed slightly inside. All these parameters may be varied to reduce the chance of accidental firing without undue experimentation. When the user wants to prick the finger of the patient, he presses the end wall 52 of the triggler against the skin of the finger. This compression force pushes clip 62 towards the proximal end of the recess and the triggler towards the proximal end of the lancet holder, increasing the compression of the spring. This causes the spring to generate an opposing extension force, which pushes against wedges 60 of the actuating ribs 56. Ribs 56 are designed to bend outwards into the firing position with this additional pressure, in which wedges 60 disengages from guiding pin 48, causing the spring to fire into a fully extended position and the lancet to jab the skin of the patient. It is clear that from the above description, the triggering mechanism is from the interaction with the patient's skin. As a result, if the patient pulls back his hand just when the user is about to press down the triggler, triggering would not occur.

The slot 108 and lug 114 at the proximal end of spring holder acts as the securing element of the spring such that after firing, the distal end of the spring recoils towards the proximal end. In this way, the sharp tip of the lancet is retracted completely back into the lancet holder after firing. This is a highly desirable safety feature.

While the present invention has been described particularly with references to the aforementioned figures, it should be understood that the figures are for illustration only and should not be taken as limitation on the invention. It is contemplated that many changes and modifications may be made by one of ordinary skill in the art without departing from the function, spirit and the scope of the invention described, examples of which are described below.

The stabilizing element in the present invention, described as side walls 68 at the four corners of the triggler 50 in above embodiment, serves not only as a structure to allow interaction between the triggler and the lancet holder, but also a structure to prevent lateral movements therebetween. As a result, only firm compressional pressure almost directly along the longitudinal axis is required for firing to occur, and accidentally knocking the triggler in any other direction is not likely to cause firing. Besides having side walls on all four corners, other embodiments may be possible, such as rigid structures symmetrically extending from the end walls of the triggler. The tight association between the triggler and the lancet holder also means that the lancet structure is completely protected and enclosed, and it is extremely difficult to dismantle the assembly without breaking some parts.

The securing element may be other structures in the molded plastic spring holder that allows interaction of the proximal end of the spring with the proximal end of the lancet holder. This securing element allows a metallic helical spring with superior springback properties to be used instead of plastic springs that may be fabricated as an integral part of the spring holder.

Besides a recess on the interior side wall of the lancet holder, other structures, such as an elongated aperture or a bracket in the side wall may also serve as the mating element. A structure which is only accessible from the interior is, however, preferred as it prevents external tampering.

What is claimed is:

1. A lancet assembly comprising:
   a lancet structure comprising:
      a body having a proximal end and a distal end and guiding elements;
      a lancet with a sharp tip, attached to said body, such that the sharp tip extend from the distal end of said body; and
      a spring coupled to and extending from tho proximal end of said body, said spring having a proximal end and a linear axis of compression;
   a lancet holder comprising:
      an open distal end;
      an end wall at a proximal end;
      side walls extending from said end wall, said side: walls having a mating element comprising recesses in the interior of said side walls;
   a spring holder having:
      an open first end,
      a second end attached to said end wall; and
      supporting structures therebetween defining an interior space, said lancet structure received within said interior space with said sharp tip proximate said open first end, said supporting structures further provided with receiving elements for engagement with said guiding elements to allow movement of said body along the axis of compression;
   a triggler, inserted into said holder, said triggler comprising:
      a triggler end wall for closing said distal end of said holder and having an aperture wherethrough said sharp distal tip of said lancet fires when triggered;
      a stabilizing element, extending from said triggler end wall and inserted between said side wails and said supporting structures for sliding movement along the axis of compression said stabilizing element further limiting movement of said triggler lateral to said axis of compression,
      a safety catch for maintaining said triggler between standby and firing positions, wherein said safety catch comprising L shaped clips extending from two opposing sides of said triggler end wall, said L-shaped clips engaging said recesses of said mating element; and
      triggering elements for engagement with said guiding elements, said triggering element in the standby position maintaining said spring in a high potential energy compressed state by forcing said guiding elements toward the proximal end of said holder, said triggering elements further movable to said firing position when a compression force is applied to said triggler end wall, said triggering elements in said firing position being disengaged from said guiding elements such that said spring is released from said compressed state and the sharp distal end of said lancet structure is fired through said aperture of said triggler end wall.

2. A lancet assembly according to claim 1, further comprising a cap for covering up said aperture.

3. A lancet assembly according to claim 1, further comprising an air-seal cap for covering up said aperture and maintaining sterility.

4. A lancet assembly according to claim 1, wherein said lancet holder further comprises a securing element connected to said proximal end of said lancet holder, for securing said proximal end of said spring to said proximal end of said lancet holder.

5. A lancet assembly according to claim 4, wherein said securing element comprises at least one lug, provided on the external surface of said spring holder proximate said end wall, for engaging an extension of said spring.

6. A lancet assembly according to claim 5, wherein said spring holder further comprises a slot along the length of said supporting structures wherethrough said extension of said spring can access said at least one lug for coupling.

7. A lancet assembly according to claim 1, wherein said guiding elements comprises a plurality of guiding pins extending laterally from at least two sides of said body.

8. A lancet assembly according to claim 1, wherein said receiving elements comprises a plurality of longitudinal slits within said supporting structure wherethrough each of said guiding pins extend.

9. A lancet assembly comprising:
   a lancet structure comprising:
      a body having a proximal end and a distal end and guiding elements;
      a lancet with a sharp tip, attached to said body, such that the sharp tip extend from the distal end of said body; and
      a spring coupled to and extending from the proximal end of said body, said spring having a proximal end and a linear axis of compression;

a lancet holder comprising:
  an open distal end; and
  an end wall at a proximal end;
  side walls extending from said end wall, said side walls having a mating element;
a spring holder having:
  an open first end,
  a second end attached to said end wall; and
  supporting structures therebetween defining an interior space, said lancet structure received within said interior space with said sharp tip proximate said open first end, said supporting structures further provided with receiving elements for engagement with said guiding elements to allow movement of said body along tie axis of compression;
a triggler, inserted into said holder, said triggler comprising:
  a triggler end wall for closing said distal end of said holder and having an aperture wherethrough said sharp distal tip of said lancet fires when triggered;
  a stabilizing element, extending from said triggler end wall and inserted between said side walls and said supporting structures for sliding movement along the axis of compression, said stabilizing element further limiting movement of said triggler lateral to said axis of compression;
  a safety catch engaging said mating element of said holder, for maintain said triggler between standby and firing positions; and
  triggering elements for engagement with said guiding elements, said triggering element in the standby position maintaining said spring in a high potential energy compressed state by forcing said guiding elements toward the proximal end of said holder, said triggering elements further movable to said firing position when a compression force is applied to said triggler end wall, said triggering elements in said firing position being disengaged from said guiding elements such that said spring is released from said compressed state and the sharp distal end of said lancet structure is fired through said aperture of said triggler end wall;
  wherein said triggering elements comprise a pair of actuating ribs with wedged ends extending from two opposing sides of said triggler end wall; and
  wherein said guiding elements comprise a pair of guiding pins extending laterally from two opposing sides of said body, said triggler inserted into said lancet holder such that said wedged ends engage said guiding pins, said actuating rib in the armed position maintaining said spring in a high potential energy compressed state by forcing said guiding pin towards the proximal end of said lancet holder, said actuating rib further bendable to said firing position when said compression force is applied to said triggler end wall.

10. A lancet assembly comprising:
a lancet structure comprising:
  a body having a proximal end and a distal end and guiding elements;
  a lancet with a sharp tip, attached to said body, such that the sharp tip extend from the distal end of said body; and
  a spring coupled to and extending from the proximal end of said body, said spring having a proximal end and a linear axis of compression;
a lancet holder comprising:
  an open distal end;
  an end wall at a proximal end; and
  side walls extending from said end wall, said side walls having a mating element compressing recesses in the interior of said side walls;
a spring holder having:
  an open first end,
  a second end attached to said end wall; and
  supporting structures therebetween defining an interior space, said lancet structure received within said interior space with said sharp tip proximate said open first end, said supporting structures further provided with receiving elements for engagement with said guiding elements to allow movement of said body along to axis of compression;
a triggler, inserted into said holder, said triggler comprising:
  a triggler end wall for closing said distal end of said holder and having an aperture wherethrough said sharp distal tip of said lancet fires when triggered;
  a stabilizing element extending from said triggler end wall and inserted between said side walls and said supporting structures for sliding movement along the axis of compression, said stabilizing element further limiting movement of said triggler lateral to said axis of compression;
  a safety catch engaging said mating element of said holder, for maintain said triggler between standby and firing positions; and
  triggering elements for engagement with said guiding element, said triggering element in the standby position maintaining said spring in a high potential energy compressed state by forcing said guiding elements toward the proximal end of said holder, said triggering elements further movable to said firing position when a compression force is applied to said triggler end wall, said triggering elements in said firing position being disengaged from said guiding elements such that said spring is released from said compressed state and the sharp distal end of said lancet structure is fired through said aperture of said triggler end wall;
  wherein said lancet holder further comprising ridges attached to said spring bolder and said lancet holder to strengthen said supporting structures.

11. A lancet assembly comprising:
a lancet structure comprising
  a body having a proximal end, a distal end and a longitudinal axis;
  a lancet having a sharp tip, said lancet attached to said body such that the lancet extend from the distal end of said body;
  a plurality of guiding pins extending laterally on opposing sides said body; and
  a helical metallic spring coupled to said body and extending from the proximal end along said longitudinal axis;
a lancet holder comprising
  an open distal end;
  an end wall at the proximal end;
  side walls extending from said end wall with two opposing side walls having a recess on the interior surface;
a holder having
  an open first end, a second end attached to and extending from said end wall; and a supporting wall therebetween defining an interior space, said lancet structure received within said interior space with said sharp tip proximate said open first end, the dimensions of said space limiting the lateral movement of said lancet structure, said supporting wall provided with slits wherethrough said guiding pins extend to allow longitudinal movement of said lancet structure;

a triggler, inserted into said holder, said triggler comprising a triggler end wall for closing said distal end of said holder; said triggler end wall substantially perpendicular to said axis of compression and having an aperture wherethrough said sharp distal tip of said lancet fires when triggered;

triggler said walls extending from said triggler end wall and inserted between said side walls of said lancet holder and said supporting wall for sliding movement along the longitudinal axis while limiting lateral movement of said triggler;

a safety catch, extending from said triggler end wall and engaging said recess of said lancet holder, for maintain said triggler inside said lancet holder between a standby position and a firing position; and a pair of actuating ribs with wedged ends, extending from said triggler end wall, for engagement with said guiding pins, said actuating ribs in the standby position maintaining said spring in a high potential energy compressed state by forcing said lancet structure towards the proximal end of said lancet holder, said actuating ribs further bendable to said firing position when a compression force is applied to said triggler end wall, said wedge in said firing position being disengaged from said guiding pins such that said spring is released from said compressed state and the sharp distal end of said lancet structure is fired through said aperture of said triggler end wall.

\* \* \* \* \*

UNITED STATES PATENT AND TRADEMARK OFFICE
CERTIFICATE OF CORRECTION

PATENT NO.     : 6,432,120 B1
DATED          : August 13, 2002
INVENTOR(S)    : Hock Meng Teo It is certified that error appears in the above-identified patent and that said Letters Patent is hereby corrected as shown below:

<u>Title page,</u>
Item [74], "*Attorney, Agent or Firm*", please add:
-- Lawrence Y.D. Ho & Associates Pte Ltd. --

Signed and Sealed this

Seventeenth Day of December, 2002

JAMES E. ROGAN
*Director of the United States Patent and Trademark Office*